(12) United States Patent
Bronstein

(10) Patent No.: US 6,514,717 B2
(45) Date of Patent: *Feb. 4, 2003

(54) KIT FOR CONDUCTING AN ASSAY TO DETECT A SUBSTANCE USING ENZYMATICALLY-INDUCED DECOMPOSITION OF DIOXETANES

(75) Inventor: Irena Y. Bronstein, Newton, MA (US)

(73) Assignee: Tropix, Inc., Beford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/960,932

(22) Filed: Sep. 25, 2001

(65) Prior Publication Data

US 2002/0102624 A1 Aug. 1, 2002

Related U.S. Application Data

(63) Continuation of application No. 09/537,693, filed on Mar. 29, 2000, now Pat. No. 6,322,727, which is a continuation of application No. 09/182,416, filed on Oct. 30, 1998, now Pat. No. 6,113,816, which is a continuation of application No. 08/767,282, filed on Dec. 16, 1996, now Pat. No. 5,866,389, which is a continuation of application No. 06/889,823, filed on Jul. 24, 1996, now abandoned.

(51) Int. Cl.$^7$ .................. G01N 33/53; G01N 33/537; C07D 35/02
(52) U.S. Cl. .................... 435/7.92; 549/510
(58) Field of Search ........................ 252/700; 435/6, 435/7.1, 7.9, 7.92; 549/333, 510, 218

(56) References Cited

U.S. PATENT DOCUMENTS

| | | |
|---|---|---|
| 2,478,377 A | 8/1949 | Dickey |
| 3,009,962 A | 11/1961 | Milas |
| 3,442,813 A | 5/1969 | Bollyky |
| 3,442,814 A | 5/1969 | Sheehan |
| 3,442,815 A | 5/1969 | Rauhut |
| 3,470,103 A | 9/1969 | Sheehan |
| 3,597,362 A | 8/1971 | Bollyky |
| 3,677,957 A | 7/1972 | Moulding |
| 3,720,622 A | 3/1973 | Bollyky |
| 3,763,188 A | 10/1973 | Krespan |
| 3,862,142 A | 1/1975 | Story |
| 4,302,534 A | 11/1981 | Halmann |
| 4,315,998 A | 2/1982 | Neckers et al. |
| 4,372,745 A | 2/1983 | Mandle |
| 4,446,233 A | 5/1984 | Auditore-Hargreave |
| 4,604,364 A | 8/1986 | Kosak |
| 4,663,278 A | 5/1987 | Dinello |
| 4,665,018 A | 5/1987 | Vold |
| 4,857,652 A | 8/1989 | Schaap |
| 4,956,477 A | 9/1990 | Brnostein et al. |
| 4,962,192 A | 10/1990 | Schaap |
| 4,978,614 A | * 12/1990 | Bronstein et al. |
| 5,177,241 A | 1/1993 | Bronstein et al. |
| 5,225,584 A | 7/1993 | Brooks et al. |
| 5,330,900 A | * 7/1994 | Bronstein et al. |
| 5,336,596 A | * 8/1994 | Bronstein et al. |
| 5,362,916 A | 11/1994 | Edwards et al. |
| 5,538,847 A | * 7/1996 | Bronstein et al. |
| 5,547,836 A | * 8/1996 | Bronstein et al. |
| 5,582,980 A | * 12/1996 | Bronstein et al. |
| 5,605,795 A | * 2/1997 | Bronstein et al. |
| 5,625,077 A | 4/1997 | Bronstein |
| 5,637,747 A | 6/1997 | Bronstein et al. |
| 5,639,907 A | 6/1997 | Bronstein et al. |
| 5,648,555 A | 7/1997 | Bronstein et al. |
| 5,654,154 A | * 8/1997 | Bronstein et al. |
| 5,679,802 A | 10/1997 | Bronstein et al. |
| 5,753,436 A | * 5/1998 | Bronstein et al. |
| 5,756,770 A | 5/1998 | Bronstein et al. |
| 5,763,681 A | 6/1998 | Edwards et al. |
| 5,777,133 A | 7/1998 | Bronstein et al. |
| 5,847,161 A | * 12/1998 | Bronstein et al. |
| 5,849,495 A | * 12/1998 | Bronstein et al. |
| 5,856,522 A | * 1/1999 | Bronstein et al. |
| 5,866,389 A | * 2/1999 | Bronstein et al. |
| 5,869,699 A | * 2/1999 | Bronstein et al. |
| 5,869,705 A | 2/1999 | Bronstein |
| RE36,536 E | * 1/2000 | Bronstein et al. |
| 6,113,816 A | * 9/2000 | Bronstein et al. |
| 6,124,478 A | * 9/2000 | Bronstein et al. |
| 6,287,767 B1 | 9/2001 | Brnostein et al. |
| 6,322,727 B1 | * 11/2001 | Bronstein et al. |

FOREIGN PATENT DOCUMENTS

| | | |
|---|---|---|
| CA | 1044639 | 12/1979 |
| FR | 2383404 | 10/1978 |
| JP | 57/042686 | 3/1982 |

OTHER PUBLICATIONS

Geller, et al., Tetrahedron Letters, 673 (1983).
Adam, et al., Chem. Ber., 116, 839 (1983).
Patolia and Trivedi, Indian J. Chem., 22B 444 (1983).
McMurry et al., J. Am. Chem. Soc., 105 pp. 1660–1661 (1983).
Schaap et al., Tetrahedron Letters, 2943 (1982).
Schaap et al., J. Amer. Chem. Soc., 104, 3504 (1982).

(List continued on next page.)

Primary Examiner—Sean McGarry
Assistant Examiner—Janet Epps
(74) Attorney, Agent, or Firm—Steven B. Kelber; Piper Rudnick LLP

(57) ABSTRACT

A kit for detecting a first substance in a sample including a stabilized 1,2-dioxetane bearing an enzyme-labile substituent, which is destabilized and caused to decompose by contacting the 1,2-dioxetane with an enzyme under conditions which cause the enzyme to cleave the enzyme-labile substituent from the dioxetane, thereby yielding a negatively charged oxygen anion bonded to the 1,2-dioxetane, which causes the 1,2-dioxetane to decompose without input from an external excitation energy source, the decomposition being accompanied by chemiluminescence; and a second component selected from the group consisting of a specific affinity substance (e.g., an antigen, an antibody or a nucleic acid probe) and an enzyme which destabilizes said 1,2-dioxetane.

17 Claims, No Drawings

OTHER PUBLICATIONS

Wynberg et al., In Bioluminescence & Chemiluminescence, DeLuca and McElroy (eds.) Academic Press, New York, p. 687 (1981).
Shimomura, et al., Photocham. Photobiol., 30, 89 (1979).
Schaap et al., J. Amer. Chem. Soc., 101, 4016 (1979).
Zaklika et al., Photochem. Photobiol., 30, 35 (1979).
McMurry et al., J. Org. Chem., vol. 43, No. 17, 3255–3266 (1978).
Zaklika et al., J. Amer. Chem. Soc., 100, 318 (1978).
Zaklika et al., J. Amer. Chem. Soc., 100, 4916 (1978).
McMurry et al., J. Org. Chem., vol. 42, No. 15, 2655–2656 (1977).
McCapra et al., J. Chem. Soc. Chem. Commun., 944 (1977).
Schaap et al., J. Amer. Chem. Soc., 99, 12790 (1977).
Corey et al., J. Amer. Chem. Soc., 94, 6190 (1972).
Wilson, et al., J. Amer. Chem. Soc., 93, 4126 (1971).
Bartlett et al., J. Amer. Chem. Soc., 92, 3223 (1970).
Mazur et al., J. Amer. Chem. Soc., 92, 3225 (1970).
Schaap et al., Organic Photochemical Synthesis, II, 49 (1976).
Schaap et al., J. Amer. Chem. Soc., 97, 7110 (1975).
Turro et al., J. Amer. Chem. Soc., 97, 7110 (1975).
Wieringa et al., Tetrahedron Letters, 169 (1972).
Kopecky et al., Can. J. Chem., 47, 709 (1969).
McCapra, F., Chem. Commun., 155 (1968).
Davies et al., J. Org. Chem., 23, 307 (1958).
Sunthankar et al., J. Org. Chem., 16, 8 (1951).
Handwritten notes from Dr. Charles Zepp, prepared sometime in Apr. 1984.
Handwritten notes from S. Stroud to C. Zepp (Polaroid Corp.), dated Jul. 2, 1984.
Handwritten notes of Dr. Charles Zepp (Polaroid dioxetane file), 1984.
Handwritten notes of Dr. Charles Zepp, 1984.
Presentation sheet, Dr. Charles Zepp (Polaroid Corp.).
Handwritten notes and data plot from Dr. A. Paul Schaap to Dr. I.Y. Bronstein, dated Nov. 13, 1985.
Disclosure and cover letter from Dr. A.P. Schaap to Donald H. Siegal, Esq., Jun. 1986.
Materials from Dr. A. Paul Schaap, Dec. 2, 1985.
Complaint: Quest systems, Inc. v. C. Zepp in Massachusetts State Court.
C. Zepp's Answer to Quest's Complaint.
Complaint: Wayne State University v. Quest Systems in Michigan State Court.
Complaint: Quest Systems v. Wayne State University in Massachusetts State Court.
Complaint: Wayne State University v. Quest Systems in U.S. District Court.
Nicolas, et al., Ann. Biol. Clin. (Paris) 43:201–5 (1985).
Handwritten notes of Paul Schaap (Jul. 20, 1983).
Hummelen et al., CA 100: 209242h (1984).
Adam et al., Tet. Lett. 23: 2835–36 (1982).
Meijer et al., Tet. Lett. 41: 3997–4000 (1979).
Wynberg et al., "1,2–Dioxetanes as Chemiluminescent Probes and Labels," in bioluminescence and chemiluminescence. Basic chemistry and Analytical applications, ed. By M.A. DeLuca et al. (1981).
Affidavit of Charles M. Zepp, submitted as attachment to paper 13 in great grandparent application 06/889,823.
Zeitschrift fur Naturforschung 39b (5), May 1984, p. 679–682 by Waldenmar Adam. Tubingen FRG Q 324.
Handley et al., Tetrahedron Lett., 3183 (1985).
Kricka, L.J., Ligand–binder Assays, Marcel Bekker, Inc., New York, p. 170 (1985).
Kricka, L.J., Ligand–Binder Assays, Marcel Dekker, Inc., New York, p. 199 (1985).

* cited by examiner

KIT FOR CONDUCTING AN ASSAY TO DETECT A SUBSTANCE USING ENZYMATICALLY-INDUCED DECOMPOSITION OF DIOXETANES

This application is a continuation application of U.S. application Ser. No. 09/537,693. Filing Date Mar. 29, 2000 U.S. Pat. No. 6,322,727, which is a continuation application of U.S. application Ser. No. 09/182,416. Filing Date Oct. 30, 1998 (U.S. Pat. No. 6,113,816), which is a continuation application of U.S. application Ser. No. 08/767,282. Filing Date Dec. 16, 1996 (U.S. Pat. No. 5,866,389), which is a continuation application of U.S. application Ser. No. 06/889,823. Filing Date Jul. 24, 1996 (abandoned), the contents of which are incorporated herein by reference.

BACKGROUND OF THE INVENTION

This invention relates to using dioxetanes to detect a substance in a sample.

Dioxetanes are compounds having a 4-membered ring in which 2 of the members are oxygen atoms bonded to each other. Dioxetanes can be thermally or photochemically decomposed to form carbonyl products, i.e., ketones or aldehydes. Release of energy in the form of light (i.e., luminescence) accompanies the decompositions.

SUMMARY OF THE INVENTION

In general, the invention features in a first aspect an improvement in an assay method in which a member of a specific binding pair (i.e., two substances which bind specifically to each other) is detected by means of an optically detectable reaction. The improvement includes the reaction, with an enzyme, of a dioxetane having the formula

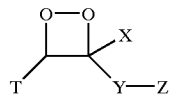

where T is a substituted (i.e., containing one or more $C_1$–$C_7$ alkyl groups or heteroatom groups, e.g., carbonyl groups) or unsubstituted cycloalkyl (having between 6 and 12 carbon atoms, inclusive, in the ring) or a polycycloalkyl (having 2 or more fused rings, each ring independently having between 5 and 12 carbon atoms, inclusive) group bonded to the 4-membered ring portion of the dioxetane by a spiro linkage; Y is a fluorescent chromophore, (i.e., Y is capable of absorbing energy to form an excited, i.e., higher energy, state, from which it emits light to return to its original energy state); X is H, a straight or branched chain alkyl group (having between 1 and 7 carbon atoms, inclusive, e.g., methyl), straight chain or branched heteroalkyl (having between 1 and 7 carbon atoms, inclusive e.g., methoxy, hydroxyethyl, or hydroxypropyl), aryl (having at least 1 ring, e.g., phenyl), heteroaryl (having at least 1 ring, e.g., pyrrolyl or pyrazolyl), cycloalkyl (having between 3 and 7 carbon atoms, inclusive, in the ring, e.g., cyclohexyl), cycloheteroalkyl (having between 2 and 7 carbon atoms, inclusive, in the ring, e.g., dioxane), aralkyl (having at least 1 ring, e.g., benzyl), or alkaryl (having at least 1 ring, e.g., tolyl), or an enzyme-cleavable group, i.e., a group having a bond which can be cleaved by an enzyme to yield an electron-rich moiety bonded to the dioxetane, e.g., phosphate, where a phosphorus-oxygen bond can be cleaved by an enzyme, e.g., acid phosphatase or alkaline phosphatase to yield a negatively charged oxygen bonded to the dioxetane; and Z is H, OH, or an enzyme-cleavable group (as defined above), provided that at least one of X or Z must be an enzyme-cleavable group, so that the enzyme cleaves the enzyme-cleavable group to form a negatively charged substituent (e.g., an oxygen anion) bonded to the dioxetane, the negatively charged substituent causing the dioxetane to decompose to form a luminescent substance (i.e., a substance that emits energy in the form of light) that includes group Y. The luminescent substance is detected as an indication of the presence of the first substance. By measuring the intensity of luminescence, the concentration of the first substance can be determined.

In preferred embodiments, one or more of groups T, X, or Y further include a solubilizing substituent, e.g., carboxylic acid, sulfonic acid, or quaternary amino salt; group T of the dioxetane is a polycycloalkyl group, preferably adamantyl; the enzyme-cleavable group includes phosphate; and the enzyme includes phosphatase.

The invention also features a kit for detecting a first substance in a sample.

In a second aspect, the invention features a method of detecting an enzyme in a sample. The method involves contacting the sample with the above-described dioxetane in which group Z is capable of being cleaved by the enzyme being detected. The enzyme cleaves group Z to form a negatively charged substituent (e.g., an oxygen anion) bonded to the dioxetane. This substituent destabilizes the dioxetane, thereby causing the dioxetane to decompose to form a luminescent substance that includes group Y of the dioxetane. The luminescent substance is detected as an indication of the presence of the enzyme. By measuring the intensity of luminescence, the concentration of the enzyme can also be determined.

The invention provides a simple, very sensitive method for detecting substances in samples, e.g., biological samples, and is particularly useful for substances present in low concentrations. Because dioxetane decomposition serves as the excitation energy source for chromophore Y, an external excitation energy source, e.g., light, is not necessary. In addition, because the dioxetane molecules are already in the proper oxidation state for decomposition, it is not necessary to add external oxidants, e.g., $H_2O_2$ or $O_2$. Enzyme-triggered decomposition allows for high sensitivity because one enzyme molecule can cause many dioxetane molecules to luminesce, thus creating an amplification effect. Moreover, the wavelength (or energy) of emission and the quantum yields of luminescence can be varied according to the choice of the Y substituent of the dioxetane (as used herein, "quantum yield" refers to the number of photons emitted from the luminescent product per number of moles of dioxetane decomposed). In addition, through appropriate modifications of the T, X, and Y groups of the dioxetane, the solubility of the dioxetane and the kinetics of dioxetane decomposition can be varied. The dioxetanes can also be attached to a variety of molecules, e.g., proteins or haptens, or immobilization substrates, e.g., polymer membranes, or included as a side group in a homopolymer or copolymer.

Other features and advantages of the invention will be apparent from the following description of the preferred embodiments thereof, and from the claims.

DESCRIPTION OF THE PREFERRED EMBODIMENTS

We now describe the structure, synthesis, and use of preferred embodiments of the invention.

Structure

The invention employs dioxetanes having the structure recited in the Summary of the Invention, above. The purpose of group T is to stabilize the dioxetane, i.e., to prevent the dioxetane from decomposing before the enzyme-cleavable group Z is cleaved. Large, bulky, sterically hindered molecules, e.g., fused polycyclic molecules, are the most effective stabilizers. In addition, T preferably contains only C—C and C—H single bonds. The most preferred molecule is an adamantyl group consisting of 3 fused cyclohexyl rings. The adamantyl group is bonded to the 4-membered ring portion of the dioxetane through a Spiro linkage.

Group Y is a fluorescent chromophore bonded to enzyme-cleavable group Z. Y becomes luminescent when an enzyme cleaves group Z, thereby creating an electron-rich moiety which destabilizes the dioxetane, causing the dioxetane to decompose. Decomposition produces 2 individual ketones, one of which contains group T, and the other of which contains groups X, Y, and Z; the energy released from dioxetane decomposition causes the Y group of the latter ketone to luminesce (if group X is H, an aldehyde is produced).

The excited state energy of chromophore Y (i.e., the energy chromophore Y must possess in order to emit light) is preferably less than the excited state energy of the ketone containing group T in order to confine luminescence to group Y. For example, when T is adamantyl, the excited state energy of chromophore Y is preferably less than the excited state energy of spiroadamantanone.

Any chromophore Y can be used according to the invention. In general, it is desirable to use a chromophore which maximizes the quantum yield in order to increase sensitivity.

Examples of suitable chromophores include the following:

1) anthracene and anthracene derivatives, e.g., 9,10-diphenylanthracene, 9-methylanthracene, 9-anthracene carboxaldehyde, anthrylalcohols and 9-phenylanthracene;
2) rhodamine and rhodamine derivatives, e.g., rhodols, tetramethyl rhodamine, tetraethyl rhodamine, diphenyldimethyl rhodamine, diphenyldiethyl rhodamine, and dinaphthyl rhodamine;
3) fluorescein and fluorescein derivatives, e.g., 5-iodoacetamido fluorescein, 6-iodoacetamido fluorescein, and fluorescein-5-maleimide;
4) eosin and eosin derivatives, e.g., hydroxy eosins, eosin-5-iodoacetamide, and eosin-5-maleimide;
5) coumarin and coumarin derivatives, e.g., 7-dialkylamino-4-methylcoumarin, 4-bromomethyl-7-methoxycoumarin, and 4-bromomethyl-7-hydroxy coumarin;
6) erythrosin and erythrosin derivatives, e.g., hydroxy erythrosins, erythrosin-5-iodoacetamide and erythrosin-5-malimide;
7) aciridine and aciridine derivatives, e.g., hydroxy aciridines and 9-methyl aciridine;
8) pyrene and pyrene derivatives, e.g., N-(1-pyrene) iodoacetamide, hydroxy pyrenes, and 1-pyrenemethyl iodoacetate;
9) stilbene and stilbene derivatives, e.g., 6,6'-dibromostilbene and hydroxy stilbenes;
10) naphthalene and naphthalene derivatives, e.g., 5-dimethylamino naphthalene-1-sulfonic acid and hydroxy naphthalene;
11) nitrobenzoxadiazoles and nitrobenzoxadiazole derivatives, e.g., hydroxy nitrobenzoxadiazoles, 4-chloro-7-nitrobenz-2-oxa-1,3-diazole, 2-(7-nitrobenz-2-oxa-1,3-diazol-4-yl) methylaminoacetaldehyde, and 6-(7-nitrobenz-2-oxa-1,3-diazol-4-yl-aminohexanoic acid;
12) quinoline and quinoline derivatives, e.g., 6-hydroxyquinoline and 6-aminoquinoline;
13) acridine and acridine derivatives, e.g., N-methylacridine and N-phenylacridine;
14) acidoacridine and acidoacridine derivatives, e.g., 9-methylacidoacridine and hydroxy-9-methylacidoacridine;
15) carbazole and carbazole derivatives, e.g., N-methylcarbazole and hydroxy-N-methylcarbazole;
16) fluorescent cyanines, e.g., DCM (a laser dye), hydroxy cyanines, 1,6-diphenyl-1,3,5-hexatriene, 1-(4-dimethyl aminophenyl)-6-phenylhexatriene, and the corresponding 1,3-butadienes;
17) carbocyanine and carbocyanine derivatives, e.g., phenylcarbocyanine and hydroxy carbocyanines;
18) pyridinium salts, e.g., 4(4-dialkyl diamino styryl) N-methyl pyridinium iodate and hydroxy-substituted pyridinium salts;
19) oxonols; and
20) resorofins and hydroxy resorofins.

The most preferred chromophores are hydroxy derivatives of anthracene or naphthalene; the hydroxy group facilitates bonding to group Z.

Group Z is bonded to chromophore Y through an enzyme-cleavable bond. Contact with the appropriate enzyme cleaves the enzyme-cleavable bond, yielding an electron-rich moiety bonded to chromophore Y; this moiety initiates the decomposition of the dioxetane into 2 individual ketones, or into a ketone and an aldehyde if group X is H. Examples of electron-rich moieties include oxygen, sulfur, and amine or amido anions. The most preferred moiety is an oxygen anion. Examples of suitable Z groups, and the enzymes specific to these groups, are given below in Table 1; an arrow denotes the enzyme-cleavable bond. The most preferred group is a phosphate ester, which is cleaved by alkaline or acid phosphatase enzymes.

TABLE 1

| Group Z | Enzyme |
|---|---|
| 1)<br><br>$^{\ominus}O-\overset{\overset{\displaystyle O\downarrow}{\|}}{\underset{\underset{\displaystyle O^{\ominus}}{\|}}{P}}-O-Y$<br><br>phosphate ester | alkaline and acid phosphatases |
| 2)<br><br>$H_3C-\overset{\overset{\displaystyle O\downarrow}{\|}}{C}-O-Y$<br><br>acetate ester | esterases |

TABLE 1-continued

| Group Z | Enzyme |
|---|---|
| 3) 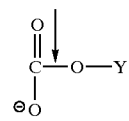 carboxyl | decarboxylases |
| 4) 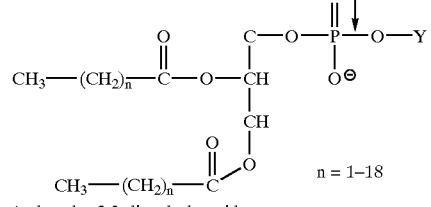 n = 1–18 <br> 1-phospho-2,3-diacyl glycerides | phospholipase D |
| 5) 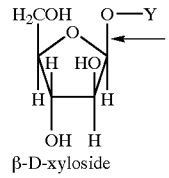 β-D-xyloside | β-xylosidase |
| 6) 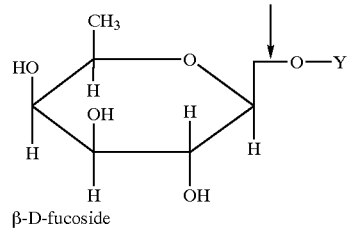 β-D-fucoside | β-D-fucosidase |
| 7) 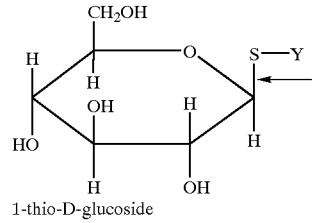 1-thio-D-glucoside | thioglucosidase |
| 8) 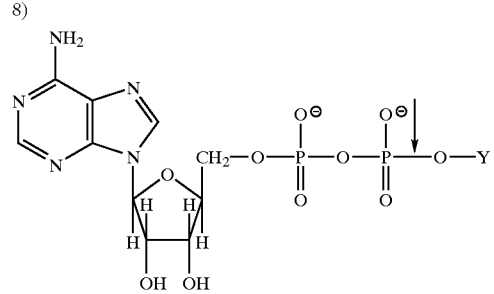 adenosine triphosphate analogs | ATPase |

TABLE 1-continued

| Group Z | Enzyme |
|---|---|
| 9) 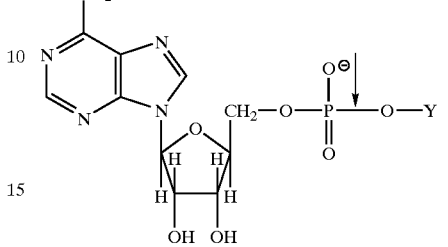 adenosine diphosphate analogs | ADPase |
| 10) 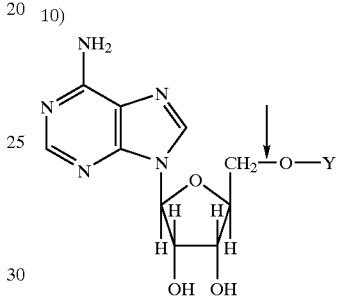 AMP analogs | 5' nucleotidase |
| 11) 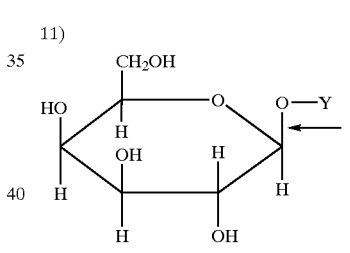 β-D-galactoside | β-D-galactosidase |
| 12) 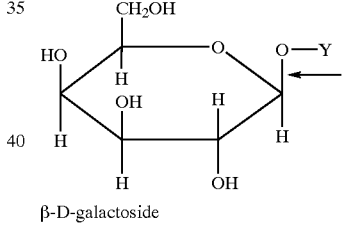 α-D-galactoside | α-D-galactosidase |
| 13) 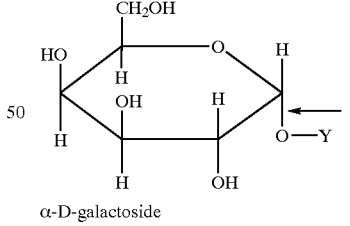 α-D-glucoside | α-D-glucosidase |

TABLE 1-continued

| Group Z | Enzyme |
|---|---|
| 14) β-D-glucoside (CH₂OH pyranose structure with O—Y) | β-D-glucosidase |
| 15) α-D-mannoside (CH₂OH pyranose structure with O—Y) | α-D-mannosidase |
| 16) β-D-mannoside (CH₂OH pyranose structure with O—Y) | β-D-mannosidase |
| 17) β-D-fructofuranoside (furanose structure with O—Y) | β-D-fructofuranosidase |
| 18) β-D-glucosiduronate (COO⁻ pyranose structure with O—Y) | β-D-glucosiduronase |
| 19) p-toluenesulfonyl-L-arginine dye ester | trypsin |
| 20) p-toluenesulfonyl-L-arginine dye amide | trypsin |

Suitable X groups are described in the Summary of the Invention, above. Preferably, X contains one or more solubilizing substituents, i.e., substituents which enhance the solubility of the dioxetane in aqueous solution. Examples of solubilizing substituents include carboxylic acids, e.g., acetic acid; sulfonic acids, e.g., methanesulfonic acid; and quaternary amino salts, e.g., ammonium bromide; the most preferred solubilizing substituent is methane-or ethane-sulfonic acid.

Preferably, the enzyme which cleaves group Z is covalently bonded to a substance having a specific affinity for the substance being detected. Examples of specific affinity substances include antibodies, e.g., anti-hCG, where the substance being detected is an antigen, e.g., hCG; antigens, e.g., hCG, where the substance being detected is an antibody, e.g., anti-hCG; or a probe capable of binding to all or a portion of a nucleic acid, e.g., DNA or RNA, being detected. Bonding is preferably through an amide bond.

Synthesis

In general, the dioxetanes of the invention are synthesized in two steps. The first step involves synthesizing an appropriately substituted olefin having the formula

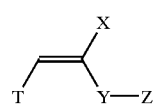

where T, X, Y, and Z are as described above. These olefins are preferably synthesized using the Wittig reaction, in which a ketone containing the T group is reacted with a phosphorus ylide (preferably based on triphenylphosphine) containing the X, Y, and Z groups, as follows:

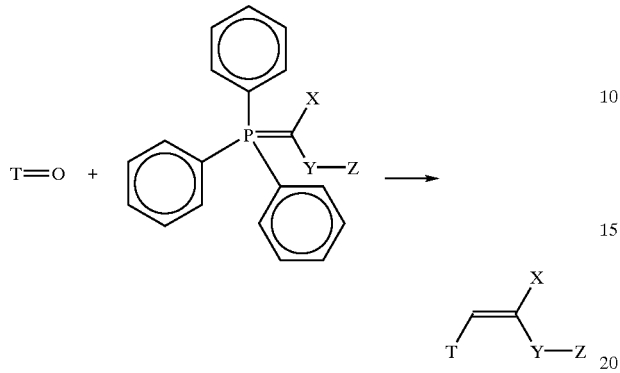

The reaction is preferably carried out at −78° C. in an ethereal solvent, e.g., tetrahydrofuran (THF).

The phosphorus ylide is prepared by reacting triphenyl phosphine with a halogenated compound containing the X, Y, and Z groups in the presence of base; examples of preferred bases include n-butyllithium, sodium amide, sodium hydride, and sodium alkoxide; the most preferred base is n-butyllithium.

The reaction sequence is as follows:

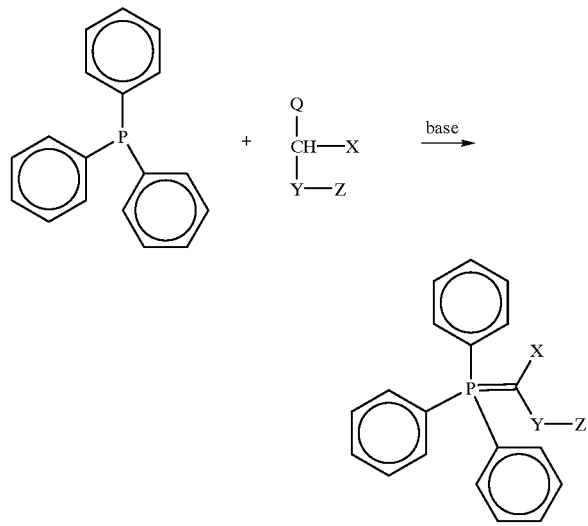

where Q is a halogen, e.g., Cl, Br, or I. The preferred halogen is Br. The reaction is preferably carried out at −78° C. in THF.

The olefin where T is adamantyl (Ad), X is methoxy ($OCH_3$), Y is anthracene (An), and Z is phosphate ($PO_4$) can be synthesized as follows.

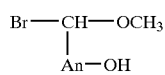

is phosphorylated by treating it with the product of phosphorus acid reacted in the presence of $HgCl_2$ with N-methylimidazole; the net result is to replace the hydroxyl group of An with a phosphate group. The phosphorylated product is then reacted with triphenylphosphine at −78° C. in THF to form the phosphorus ylide having the formula

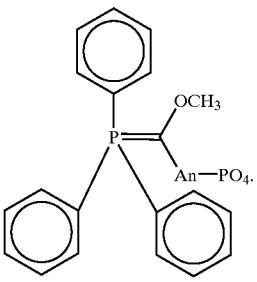

The reaction is conducted in a dry Ar atmosphere. Spiroadamantanone (Ad=O) is then added to the solution containing the ylide, while maintaining the temperature at −78° C., to form the olefin having the formula

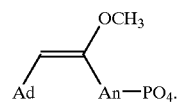

The olefin is then purified using conventional chromatography methods.

The second step in the synthesis of the dioxetanes involves converting the olefin described above to the dioxetane. Preferably, the conversion is effected photochemically by treating the olefin with singlet oxygen ($^1O_2$) in the presence of light. $^1O_2$ adds across the double bond to form the dioxetane as follows:

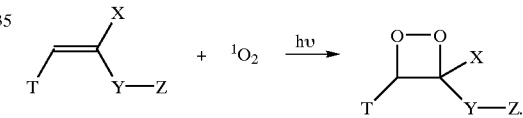

The reaction is preferably carried out at −78° C. in a halogenated solvent, e.g., methylene chloride. $^1O_2$ is generated using a photosensitizer. Examples of photosensitizers include polymer-bound Rose Bengal (commercially known as Sensitox I and available from Hydron Laboratories, New Brunswick, N.J.) and methylene blue (a well-known dye and pH indicator). The most preferred sensitizer is Rose Bengal.

The synthesis of the dioxetane having the formula

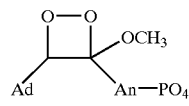

follows.

The olefin having the formula

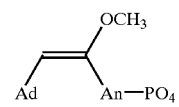

is dissolved in methylene chloride, and the solution is placed in a 2-cm² pyrex tube equipped with a glass paddle; the paddle is driven from above by an attached, glass enclosed, bar magnet. The solution is cooled to −78° C. and 1 g of polymer-bound Rose Bengal is added with stirring. Oxygen is then passed over the surface of the agitated solution while the reaction tube is exposed to light from a 500 W tungsten-halogen lamp (GE Q500 Cl) equipped with a UV-cut off filter (Corning 3060: transmission at 365 nm=0.5%). Thin layer chromatography (tlc) is used to monitor the disappearance of the olefin and the concurrent appearance of the dioxetane. After the reaction is complete (as indicated by tlc), the solvent is removed and the dioxetane is isolated.

Use

A wide variety of assays exist which use visually detectable means to determine the presence or concentration of a particular substance in a sample. The above-described dioxetanes can be used in any of these assays. Examples of such assays include immunoassays to detect antibodies or antigens, e.g., $\alpha$ or $\beta$-hCG; enzyme assays; chemical assays to detect, e.g., potassium or sodium ions; and nucleic acid assays to detect, e.g., viruses (e.g., HTLV III or cytomegalovirus, or bacteria (e.g., *E. Coli*)).

When the detectable substance is an antibody, antigen, or nucleic acid, the enzyme capable of cleaving group Z of the dioxetane is preferably bonded to a substance having a specific affinity for the detectable substance (i.e., a substance that binds specifically to the detectable substance), e.g., an antigen, antibody, or nucleic acid probe, respectively. Conventional methods, e.g., carbodiimide coupling, are used to bond the enzyme to the specific affinity substance; bonding is preferably through an amide linkage.

In general, assays are performed as follows. A sample suspected of containing a detectable substance is contacted with a buffered solution containing an enzyme bonded to a substance having a specific affinity for the detectable substance. The resulting solution is incubated to allow the detectable substance to bind to the specific affinity portion of the specific affinity-enzyme compound. Excess specific affinity-enzyme compound is then washed away, and a dioxetane having a group Z that is cleavable by the enzyme portion of the specific affinity-enzyme compound is added. The enzyme cleaves group Z, causing the dioxetane to decompose into 2 ketones (or an aldehyde and a ketone when group X is H); chromophore Y bonded to one of the ketones is thus excited and luminesces. Luminescence is detected using, e.g., a cuvette or camera luminometer, as an indication of the presence of the detectable substance in the sample. Luminescence intensity is measured to determine the concentration of the substance.

When the detectable substance is an enzyme, a specific affinity substance is not necessary. Instead, a dioxetane having a Z group that is cleavable by the enzyme being detected is used. Therefore, an assay for the enzyme involves adding the dioxetane to the enzyme-containing sample, and detecting the resulting luminescence as an indication of the presence and the concentration of the enzyme.

Examples of specific assays follow.

A. Assay for Human IgG

A 96-well microtiter plate is coated with sheep anti-human IgG (F(ab)$_2$ fragment specific). A serum sample containing human IgG is then added to the wells, and the wells are incubated for 1 hr. at room temperature. Following the incubation period, the serum sample is removed from the wells, and the wells are washed four times with an aqueous buffer solution containing 0.15M NaCl, 0.01M phosphate, and 0.1% bovine serum albumin (pH 7.4).

Alkaline phosphatase bonded to anti-human IgG is added to each well, and the wells are incubated for 1 hr. The wells are then washed four times with the above buffer solution, and a buffer solution of a phosphate-containing dioxetane is added. The resulting luminescence caused by enzymatic degradation of the dioxetane is detected in a luminometer, or with photographic film in a camera luminometer.

B. Assay for hCG

Rabbit anti-$\alpha$ hCG is adsorbed onto a nylon-mesh membrane. A sample solution containing hCG, e.g., urine from a pregnant woman, is blotted through the membrane, after which the membrane is washed with 1 ml of a buffer solution containing 0.15M NaCl, 0.01M phosphate, and 0.1% bovine serum albumin (pH 7.4).

Alkaline phosphatase-labelled anti-$\beta$-hCG is added to the membrane, and the membrane is washed again with 2 ml of the above buffer solution. The membrane is then placed in the cuvette of a luminometer or into a camera luminometer, and contacted with a phosphate-containing dioxetane. The luminescence resulting from enzymatic degradation of the dioxetane is then detected.

C. Assay for Serum Alkaline Phosphatase 2.7 ml of an aqueous buffer solution containing 0.84M 2-methyl-2-aminopropanol is placed in a 12×75 mm pyrex test tube, and 0.1 ml of a serum sample containing alkaline phosphatase added. The solution is then equilibrated to 30° C. 0.2 ml of a phosphate-containing dioxetane is added, and the test tube immediately placed in a luminometer to record the resulting luminescence. The level of light emission will be proportional to the rate of alkaline phosphatase activity.

D. Nucleic Acid Hybridization Assay

A sample of cerebrospinal fluid (CSF) suspected of containing cytomegalovirus is collected and placed on a nitrocellulose membrane. The sample is then chemically treated with urea or guanidinium isothiocyanate to break the cell walls and to degrade all cellular components except the viral DNA. The strands of the viral DNA thus produced are separated and attached to the nitrocellulose filter. A DNA probe specific to the viral DNA and labelled with alkaline phosphatase is then applied to the filter; the probe hybridizes with the complementary viral DNA strands. After hybridization, the filter is washed with an aqueous buffer solution containing 0.2M NaCl and 0.1 mM Tris-HCl (pH= 8.0) to remove excess probe molecules. A phosphate-containing dioxetane is added and the resulting luminescence from the enzymatic degradation of the dioxetane is measured in a luminometer or detected with photographic film.

Other embodiments are within the following claims.

For example, the enzyme-cleavable group Z can be bonded to group X of the dioxetane, instead of group Y. The specific affinity substance can be bonded to the dioxetane through groups X, Y, or T (preferably group X), instead of the enzyme. In this case, the group to which the specific affinity substance is bonded is provided with, e.g., a carboxylic acid, amino, or maleimide substituent to facilitate bonding.

Groups X, Y, or T of the dioxetane can be bonded to a polymerizable group, e.g., a vinyl group, which can be polymerized to form a homopolymer or copolymer.

Groups X, Y, or T of the dioxetane can be bonded to, e.g., membranes, films, beads, or polymers for use in immuno- or nucleic acid assays. The groups are provided with, e.g., carboxylic acid, amino, or maleimide substituents to facilitate bonding.

Groups X, Y, or T of the dioxetane can contain substituents which enhance the kinetics of the dioxetane enzymatic degradation, e.g., electron-rich moieties (e.g., methoxy).

Groups Y and T of the dioxetane, as well as group X, can contain solubilizing substituents.

Appropriately substituted dioxetanes can be synthesized chemically, as well as photochemically. For example, the olefin prepared from the wittig reaction can be epoxidized using a peracid, e.g., p-nitroperbenzoic acid. The epoxidized olefin can then be converted to the dioxetane by treatment with an ammonium salt, e.g., tetramethylammonium hydroxide.

Another example of a chemical synthesis involves converting the olefin prepared from the Wittig reaction to a 1,2 bromohydroperoxide by reacting the olefin with $H_2O_2$ and dibromantin (1,3-dibromo-5,5-dimethyl hydantoin). Treatment of the 1,2-bromohydroperoxide with base, e.g., OH or silver salts, e.g., silver bromide, forms the dioxetane.

Olefin precursors for the dioxetane can be synthesized by reacting a ketone with a perester in the presence of $TiCl_3$ and lithium aluminum hydride (LAH). For example, to synthesize an olefin where T is adamantyl (Ad), X is methoxy ($OCH_3$), Y is anthracene (An), and Z is phosphate ($PO_4$), the following reaction sequence is used:

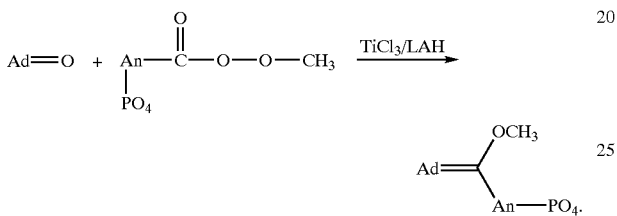

To phosphorylate chromophore Y, e.g., anthracene, a hydroxyl derivative of the chromophore, e.g., hydroxy anthracene, can be reacted with a cyclic acyl phosphate having the following formula:

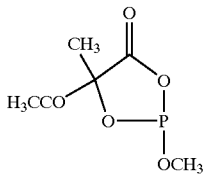

The reaction product is then hydrolyzed with water to yield the phosphorylated chromophore. The cyclic acyl phosphate is prepared by reacting 2,2,2-trimethoxy-4,5-dimethyl-1,3-dioxaphospholene with phosgene at 0° C., following by heating at 120° C. for 2 hr.

What is claimed is:

1. A kit for detecting a first substance in a sample, comprising:
   (1) a stabilized 1,2-dioxetane bearing an enzyme-labile substituent, wherein the 1,2-dioxetane can be destabilized and caused to decompose by contact with an enzyme under conditions which cause said enzyme to cleave said enzyme-labile substituent from said dioxetane, yielding a negatively charged oxygen anion which undergoes decomposition without input from an external excitation energy source, said decomposition being accompanied by chemiluminescence; and
   (2) a specific affinity substance selected from the group consisting of an antigen, an antibody and a nucleic acid probe.

2. The kit of claim 1, wherein said specific affinity substance is selected from the group consisting of an antigen, an antibody and a nucleic acid probe.

3. The kit of claim 2, wherein said specific affinity substance is bonded directly to said 1,2-dioxetane.

4. A kit for detecting a first substance in a sample, comprising:
   (1) a stabilized 1,2-dioxetane having the formula

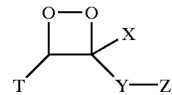

wherein T is a cycloalkyl or polycycloalkyl group bonded to the 4-membered ring portion of said dioxetane by a Spiro linkage; Y is a fluorescent chromophore; X is H, alkyl, aryl, aralkyl, alkaryl, heteroalkyl, heteroaryl, cycloalkyl, cycloheteroalkyl, or an enzyme-cleavable group; and Z is H or an enzyme-cleavable group, provided that at least one of X or Z must be an enzyme-cleavable group; and
   wherein said 1,2-dioxetane bears an enzyme-labile substituent which is destabilized and caused to decompose by contacting said 1,2-dioxetane with an enzyme under conditions which cause said enzyme to cleave said enzyme-labile substituent from said dioxetane, yielding a negatively charged oxygen anion bonded to said 1,2-dioxetane, which causes said 1,2-dioxetane to decompose without input from an external excitation energy source, said decomposition being accompanied by chemiluminescence; and
   (2) a second component selected from the group consisting of a specific affinity substance and an enzyme, wherein said specific affinity substance is selected from the group consisting of an antigen, an antibody and a nucleic acid probe.

5. The kit of claim 4, wherein T is an adamantyl group.

6. The kit of claim 5, wherein said adamantyl group bears a solubilizing substituent.

7. The kit of claim 4, wherein Z is selected from the group consisting of a phosphate ester, an acetate ester, a carboxyl group, a 1-5phospho-2,3-diacyl glyceride, β-D-xyloside, β-D-fucoside, 1-thio-D-glucoside, an adenosine triphosphate analog, an adenosine diphosphate analog, an adenosine monophosphate analog, β-D-galactoside, α-D-galactoside, α-D-glucoside, β-D-glucoside, α-D-mannoside, β-D-mannoside, β-D-fructofuranoside, β-D-glucosiduronate, P-toluenesulfonyl-L-arginine diester and P-toluenesulfonyl-L-arsinine diamide.

8. The kit of claim 4, wherein X is selected from the group consisting of hydrogen, methoxy, hydroxyethyl, hydroxypropyl, phenyl, pyrolyl, pyrazoylyl, cyclohexyl, dioxane, benzyl, tolyl and an enzyme-cleavable group.

9. The kit of claim 4, wherein said fluorescent chromophore Y is an aryl moiety.

10. The kit of claim 4, wherein said specific affinity substance is selected from the group consisting of an antibody, an antigen, a probe capable of binding to a portion of nucleic acid and mixtures thereof.

11. The kit of claim 4, wherein at least one of said moieties X, Y and T bear a solubilizing substituent.

12. The kit of claim 4, wherein at least one of said moieties X, Y and T bears a substituent which enhance kinetics of dioxetane decomposition.

13. The kit of claim 4, wherein said kit further comprises a membrane, film, bead or polymer.

14. The kit of claim 4, wherein said enzyme is selected from the group consisting of alkaline phosphatase, acid phosphatase, esterase, decarboxylase, phospholipase D, β-xylosidase, β-D-fucosidase, thioglucosidase, ATPase, ADPase, 5'nucleotidase, β-D-galactosidase, α-D-galactosidase, α-D-glucosidase, β-D-glucosidase, α-D-mannosidase, β-D-mannosidase, β-D-fructofuronase, β-D-glucosiduronase and trypsin.

15. The kit of claim 4, wherein said specific affinity substance is bonded directly to said 1,2-dioxetane.

16. A kit for detecting a first substance in a sample, comprising:
(1) at least two stabilized 1,2-dioxetanes having the formula

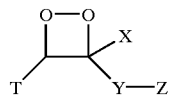

wherein T is a cycloalkyl or polycycloalkyl group bonded to the 4-membered ring portion of said dioxetane by a spiro linkage; Y is a fluorescent chromophore; X is H, alkyl, aryl, aralkyl, alkaryl, heteroalkyl, heteroaryl, cycloalkyl, cycloheteroalkyl, or an enzyme-cleavable group; and Z is H or an enzyme-cleavable group, provided that at least one of X or Z must be an enzyme-cleavable group and said at least two dioxetanes include different Z moieties; and wherein said 1,2-dioxetanes bear enzyme-labile substituents which are destabilized and caused to decompose by contacting said 1,2-dioxetanes with at least one enzyme under conditions which cause said enzyme to cleave said enzyme-labile substituents from said dioxetanes, yielding negatively charged oxygen anions bonded to said 1,2-dioxetanes, which causes said 1,2-dioxetanes to decompose without input from an external excitation energy source, said decomposition being accompanied by chemiluminescence; and (2) a second component selected from the group consisting of a specific affinity substance and an enzyme, said specific affinity substance being selected from the group consisting of an antigen, an antibody and a nucleic acid probe.

17. The kit of claim 16, wherein said kit further comprises at least two separate enzymes, one of which cleaves said enzyme-cleavable group of a first dioxetane and the remaining-enzyme cleaves said enzyme-cleavable group of a second dioxetane.

* * * * *